United States Patent
Hoffmann et al.

(10) Patent No.: US 10,640,538 B2
(45) Date of Patent: May 5, 2020

(54) PHENYLALANINE-FREE PROTEIN FOR THE TREATMENT OF PKU

(71) Applicant: METAX INSTITUT FÜR DIÄTETIK GMBH, Friedberg/Hessen (DE)

(72) Inventors: Bernhard Hoffmann, Rosbach v.d.H. (DE); Yvonne Mücke, Wöllstadt (DE); Stefan Rasche, Aachen (DE); Natalia Jablonka, Düren (DE); Stefan Schillberg, Aachen (DE)

(73) Assignee: METAX INSTITUT FÜR DIÄTETIK GMBH, Friedberg/Hessen (DE)

( * ) Notice: Subject to any disclaimer, the term of this patent is extended or adjusted under 35 U.S.C. 154(b) by 0 days.

(21) Appl. No.: 16/329,027

(22) PCT Filed: Aug. 30, 2017

(86) PCT No.: PCT/EP2017/071814
§ 371 (c)(1),
(2) Date: Feb. 27, 2019

(87) PCT Pub. No.: WO2018/041920
PCT Pub. Date: Mar. 8, 2018

(65) Prior Publication Data
US 2019/0202872 A1    Jul. 4, 2019

(30) Foreign Application Priority Data

Sep. 1, 2016 (EP) .................................. 16186895

(51) Int. Cl.
| | | |
|---|---|---|
| *A61K 9/00* | (2006.01) |
| *A61K 38/16* | (2006.01) |
| *A61K 38/10* | (2006.01) |
| *A61K 38/45* | (2006.01) |
| *G01N 33/68* | (2006.01) |
| *C07K 14/32* | (2006.01) |
| *A23L 33/195* | (2016.01) |
| *A61P 3/00* | (2006.01) |
| *A61K 38/00* | (2006.01) |

(52) U.S. Cl.
CPC .......... *C07K 14/32* (2013.01); *A23L 33/195* (2016.08); *A61P 3/00* (2018.01); *A23V 2002/00* (2013.01); *A23V 2250/54* (2013.01); *A61K 38/00* (2013.01); *C07K 2319/21* (2013.01)

(58) Field of Classification Search
CPC .......... C12Y 207/04003; A61K 38/164; A61K 38/10; A61K 38/16; A61K 38/45; A61K 9/0095; A61K 9/0053; G01N 33/6806
See application file for complete search history.

(56) References Cited

U.S. PATENT DOCUMENTS

| | | |
|---|---|---|
| 6,004,930 A | 12/1999 | Hainline |
| 6,495,344 B1 | 12/2002 | Carr et al. |
| 2008/0269070 A1 | 10/2008 | Ramseier et al. |
| 2015/0307562 A1 | 10/2015 | Basu et al. |

FOREIGN PATENT DOCUMENTS

| | | |
|---|---|---|
| WO | WO 95/02692 A1 | 1/1995 |
| WO | WO 2013/148332 A1 | 10/2013 |
| WO | WO 2016/046234 A2 | 3/2016 |

OTHER PUBLICATIONS

General stress protein 16O (G16O_BACSU), "UniProtKB—P80872 (G16O_BACSU)," accessed online at <uniprot.org/uniprot/P80872> (Feb. 27, 2019).
International Bureau, International Search Report and Written Opinion in International Application No. PCT/EP2017/071814, dated Oct. 12, 2017.
Piotrzkowski et al., "Tackling heterogeneity: a leaf disc-based assay for the high-throughput screening of transient gene expression in tobacco.," *PLoS One*, 7(9): e45803 (2012).
Rasche et al., "One-Step Protein Purification: Use of a Novel Epitope Tag for Highly Efficient Detection and Purification of Recombinant Proteins," *The Open Biotechnology Journal*, 5: 1-6 (2011).
Seagraves et al., "Cardiac Teratogenicity in Mouse Maternal Phenylketonuria: Defining phenotype parameters and genetic background influences," *Mol. Genet. Metab.*, 107(4): 650-658 (2012).
Shedlovsky et al., "Mouse models of human phenylketonuria," *Genetics*, 134(4): 1205-1210 (1993).
Soltanizadeh et al., "Strategies Used in Production of Phenylalanine-Free Foods for PKU Management," *Comprehensive Rev. Food Sci. and Food Safety*, 13: 287-299 (2014).

*Primary Examiner* — Maryam Monshipouri
(74) *Attorney, Agent, or Firm* — Leydig, Voit & Mayer, Ltd.

(57) ABSTRACT

A recombinant dietary protein is provided that is free of phenylalanine and is a dietary protein with a high biological value. Further provided are a vector encoding said dietary protein, a microorganisms expressing said protein, a method for the production of said protein, and a dietary composition comprising said protein that in an embodiment is for use as a medicament and/or food for special medical purposes in patients with accumulations of phenylalanine in the body.

18 Claims, 4 Drawing Sheets

Specification includes a Sequence Listing.

| G1.1 standard mouse diet | G2.1 Phe-free GSP105 protein diet | G3.2 Phe-free amino acid diet |

SEQUENCE LISTING

<160> NUMBER OF SEQ ID NOS: 7

<210> SEQ ID NO 1
<211> LENGTH: 168
<212> TYPE: PRT
<213> ORGANISM: Bacillus subtilis

<400> SEQUENCE: 1

```
Met Ala Leu Thr Lys Glu Gln Thr Gln His Leu Tyr His Lys Leu Leu
1               5                   10                  15

Asp Met Gln Lys Glu Leu Ser Gly Glu Lys Lys Glu Thr Glu Ser Met
            20                  25                  30

Thr Glu Glu Val Gly Glu Leu Ser Asn Gly Val Asp Asn His Met Ala
        35                  40                  45

Asp His Gly Thr Leu Val Thr Asp Arg Met Thr Asp Gln Thr Val Lys
    50                  55                  60

Glu Ile Asp Arg Glu Leu Leu Glu Val Asn Arg Ala Leu Gln Lys
65                  70                  75                  80

Met Lys Asp Gly Thr Tyr Gly Val Cys Glu Lys Thr Gly Gln Glu Ile
                85                  90                  95

Pro Tyr Glu Arg Leu Glu Ala Val Pro Tyr Ala Arg Met Thr Val Glu
            100                 105                 110

Ala Gln Ala Asp Val Glu Asp Leu Glu Thr Asp Ala Pro Ser Tyr
            115                 120                 125

Glu Arg Glu Phe His Gln Val Lys Asp Leu Ser Asn Lys Glu Thr
            130                 135                 140

Ile Asp Gln Lys Ser Ser Gln Thr Tyr Glu Ile Leu Asp Arg Glu Gln
145                 150                 155                 160

Asp Ser Lys Ala Ala Ala Ser Arg
                165
```

<210> SEQ ID NO 2
<211> LENGTH: 168
<212> TYPE: PRT
<213> ORGANISM: Artificial Sequence
<220> FEATURE:
<223> OTHER INFORMATION: GSP105

<400> SEQUENCE: 2

```
Met Ala Leu Thr Lys Glu Gln Thr Gln His Leu Tyr His Lys Leu Leu
1               5                   10                  15

Asp Met Gln Lys Glu Leu Ser Gly Glu Lys Lys Glu Thr Glu Ser Met
            20                  25                  30

Thr Glu Glu Val Gly Glu Leu Ser Asn Gly Val Asp Asn His Met Ala
        35                  40                  45

Asp His Gly Thr Leu Val Thr Asp Arg Met Thr Asp Gln Thr Val Lys
    50                  55                  60

Glu Ile Asp Arg Glu Leu Leu Glu Val Asn Arg Ala Leu Gln Lys
65                  70                  75                  80

Met Lys Asp Gly Thr Tyr Gly Val Cys Glu Lys Thr Gly Gln Glu Ile
                85                  90                  95

Pro Tyr Glu Arg Leu Glu Ala Val Pro Tyr Ala Arg Met Thr Val Glu
            100                 105                 110

Ala Gln Ala Asp Val Glu Asp Leu Glu Thr Asp Ala Pro Ser Tyr
            115                 120                 125

Glu Arg Glu Trp His Gln Val Lys Asp Leu Ser Asn Lys Glu Thr
            130                 135                 140
```

```
Ile Asp Gln Lys Ser Ser Gln Thr Tyr Glu Ile Leu Asp Arg Glu Gln
145                 150                 155                 160

Asp Ser Lys Ala Ala Ala Ser Arg
                165
```

<210> SEQ ID NO 3
<211> LENGTH: 6
<212> TYPE: PRT
<213> ORGANISM: Artificial Sequence
<220> FEATURE:
<223> OTHER INFORMATION: epitope from Tag54

<400> SEQUENCE: 3

```
Lys Asp Trp Glu His Leu
1               5
```

<210> SEQ ID NO 4
<211> LENGTH: 12
<212> TYPE: PRT
<213> ORGANISM: Artificial Sequence
<220> FEATURE:
<223> OTHER INFORMATION: Tag54 with a Phe-->Ala substitution

<400> SEQUENCE: 4

```
Lys His Ile Lys Asp Trp Glu His Leu Glu Glu Ala
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: Tag54 with a Phe-->Tyr substitution

<400> SEQUENCE: 5

```
Lys His Ile Lys Asp Trp Glu His Leu Glu Glu Tyr
1               5                   10
```

<210> SEQ ID NO 6
<211> LENGTH: 186
<212> TYPE: PRT
<213> ORGANISM: Artificial Sequence
<220> FEATURE:
<223> OTHER INFORMATION: GSP105-6His-Tag54P15

<400> SEQUENCE: 6

```
Met Ala Leu Thr Lys Glu Gln Thr Gln His Leu Tyr His Lys Leu Leu
1               5                   10                  15

Asp Met Gln Lys Glu Leu Ser Gly Glu Lys Lys Glu Thr Glu Ser Met
                20                  25                  30

Thr Glu Glu Val Gly Glu Leu Ser Asn Gly Val Asp Asn His Met Ala
            35                  40                  45

Asp His Gly Thr Leu Val Thr Asp Arg Met Thr Asp Gln Thr Val Lys
        50                  55                  60

Glu Ile Asp Arg Glu Leu Leu Glu Val Asn Arg Ala Leu Gln Lys
65                  70                  75                  80

Met Lys Asp Gly Thr Tyr Gly Val Cys Glu Lys Thr Gly Gln Glu Ile
                85                  90                  95

Pro Tyr Glu Arg Leu Glu Ala Val Pro Tyr Ala Arg Met Thr Val Glu
            100                 105                 110

Ala Gln Ala Asp Val Glu Asp Leu Glu Thr Asp Ala Pro Ser Tyr
        115                 120                 125
```

```
Glu Arg Glu Trp His Glu Gln Val Lys Asp Leu Ser Asn Lys Glu Thr
    130                 135                 140

Ile Asp Gln Lys Ser Ser Gln Thr Tyr Glu Ile Leu Asp Arg Glu Gln
145                 150                 155                 160

Asp Ser Lys Ala Ala Ala Ser Arg His His His His His Lys His
            165                 170                 175

Ile Lys Asp Trp Glu His Leu Glu Glu Ala
            180                 185

<210> SEQ ID NO 7
<211> LENGTH: 558
<212> TYPE: DNA
<213> ORGANISM: Artificial Sequence
<220> FEATURE:
<223> OTHER INFORMATION: G105-6His-Tag54-P15 (B. subtilis)

<400> SEQUENCE: 7
atggcactga caaaagaaca aacgcaacat ctgtatcata aactgcttga catgcaaaaa      60
gaactgagcg gagaaaagaa agaaacggaa tcaatgacag aagaagtcgg tgaattaagc    120
aatggcgtag ataaccatat ggccgatcat ggcacattgg ttacggatcg tatgacagac    180
caaacggtga agaaattga tagagaactg cttgaagaag tcaatcgcgc attacaaaaa    240
atgaaagatg gcacatatgg agtatgcgaa aaaacgggtc aggaaatccc gtatgaacgt    300
ttagaagcgg tcccttacgc tcggatgaca gttgaagccc aagcagatgt ggaagatgac    360
ttggaaacgg acgcaccgtc ttatgaacgc gaatggcatg aacaggtgaa agatctgtcc    420
aacaaagaaa caattgacca aaaatcaagc cagacgtacg aaatccttga tagagaacag    480
gactctaaag cggccgcttc tagacatcat catcatcatc ataaacatat caaagactgg    540
gaacatctgg aagaagcc                                                   558
```

PHENYLALANINE-FREE PROTEIN FOR THE TREATMENT OF PKU

CROSS-REFERENCE TO RELATED APPLICATIONS

This patent application is the U.S. national stage of PCT/EP2017/071814, filed Aug. 30, 2017, which claims the benefit of European Patent Application No. 16186895.5, filed Sep. 1, 2016, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 6,542 Byte ASCII (Text) file named "741919.TXT," dated Aug. 30, 2017.

TECHNICAL FIELD

The invention relates to a recombinant dietary protein or a dietarily sufficient portion thereof wherein said protein comprises no phenylalanine for use in the diet of patients affected by phenylketonuria.

BACKGROUND OF THE INVENTION

Phenylketonuria (PKU) (OMIM 261600, ORPHA716) is an inherited metabolic disorder with an incidence of 1:10,000 in Europe. In most cases, this is an amino acid metabolism disorder resulting from an absent or impaired function of the liver enzyme phenylalanine hydroxylase (PAH). Deficiencies in PAH in turn result in an excess of phenylalanine (Phe) in the brain and plasma. The deficiency in PAH ultimately manifests in a lack of tyrosine, which is a precursor for neurotransmitters. Together with mutations involving enzymes of the pterin metabolism, PKU is associated with hyperphenylalaninemia (HPA).

The disease is commonly diagnosed in most countries right after birth during newborn screenings due to elevated blood Phe levels. Left undetected and untreated early in life, PKU leads to irreversible damage of the infant's nervous system, severe mental retardation and poor brain development. Features other than intellectual disabilities in untreated patients include neurological complications, neuropsychological impairments as well as executive function deficits. It has been reported that when left untreated an infant suffers a loss of IQ within the first year of infancy. Depending on the age at start of treatment, the blood Phe levels during different age periods and the compliance of the dietary therapy PKU is invariably accompanied by at least some loss of IQ. Once detected, the condition is treated by providing the infant, and later the child, with a Phe-restricted diet. In adults, the protein supplements routinely taken by classic PKU patients are Phe-free with the assumption that such adults will receive sufficient quantities of Phe through the remaining diet, controlled under a strict regimen, so that the overall diet is a low Phe diet. In particular, pregnant women who suffer from the condition are recommended to comply with a rigid Phe-limited dietary regimen to avoid the risk of impairment of the development of the foetus and congenital malformation (maternal PKU syndrome).

In more recent years it has been shown that pathological symptoms which manifest from the condition of excess of Phe, collectively termed hyperphenylalaninemia (HPA), may be divided into multiple discrete disorders, which are diagnosed according to plasma Phe concentrations and responsiveness to a co-factor for PAH. At an initial level, HPAs may be divided into HPA caused as a result of a deficiency in the cofactor 6R-L-erythro-5,6,7,8-tetrahydrobiopterin (BH4) due to enzymatic defects in the biopterin metabolism (malignant PKU) and HPA resulting from a deficiency in PAH. The latter is further subdivided resulting in at least four sub-categories depending on the plasma concentration of Phe in the absence of dietary or other therapeutic intervention (referred to herein as "unrestricted plasma Phe concentration") and the responsiveness to the co-factor BH4.

Normal plasma Phe homeostasis is tightly controlled resulting in a plasma Phe concentration of 60 µmol/L±15 µmol/L. Classical PKU (ORPHA79254) is the most severe form of PKU and it results from null or severe mutations in PAH, which lead to unrestricted plasma Phe concentrations greater than 1200 µmol/L when left untreated. Individuals with classical (or severe) PKU must be treated with a strict dietary regimen that is based on a very low Phe diet in order to reduce their Phe concentrations to a safe range. Milder forms of PKU also have been characterized. A less severe form of PKU is one which manifests in unrestricted plasma Phe concentrations of 10-20 mg/dL (600-1200 µmol/L) and is generally termed "mild PKU" (ORPHA79253). This moderate form of PKU is managed through the use of moderate dietary restrictions, e.g., a comparatively low-protein diet without the need of a supplementation with Phe-free amino acid formulas. Mild HPA, also referred to as benign or non-PKU-HPA (ORPHA79651) is characterized by unrestricted plasma Phe concentrations of between 180-600 µmol/L. The individuals with non-PKU-HPA are not routinely treated as they are considered to have plasma Phe levels that are within the "safe" range. In dietary PKU therapy, a range below <360 µmol/L is aimed for, with a range up to 600 µmol/L considered acceptable. Finally, BH4-responsive PKU/HPA (ORPHA293284) is characterised by unrestricted plasma Phe concentrations of >360 µmol/L which can be markedly reduced or normalized after oral loading with tetrahydrobiopterin (BH4; sapropterin dihydrochloride). This mild to moderate form of PKU/HPA is caused by specific mutations in the PAH gene leading to mutant proteins with significant residual enzymatic activity. Supplementation of BH4 as part of the PKU/HPA management enables some patients to relax their Phe-restricted dietary regimen. It is to be understood that the terms "treatment of PKU" or "PKU patient" as used herein are intended to refer to the treatment of and patients with the following forms of HPA, e.g. classical PKU, mild PKU, mild HPA and BH4-responsive PKU/HPA.

At the beginning of the dietary PKU therapy in the early 1950ies, patients have been provided with the essential amino acids (except Phe) by protein hydrolysates. Therefore, a protein with relatively high levels of essential amino acids, such as casein (a protein commonly found in mammalian milk, making up 80% of the proteins in cow milk) or bovine serum albumin was hydrolysed followed by a filtration step of the peptides to remove as much Phe contamination as possible, and/or by combining free amino acids in a mixture that includes a hydrolysed protein. Today, typically balanced mixtures of free crystalline amino acids comprising essential amino acids (except Phe) are provided to the patients. Such amino acid mixtures may have a bitter taste, cause a sandy mouthfeel and may be deemed unsuitable or undesirable for certain uses. As a result, such mixtures sometimes include flavours to mask the taste of the free amino acids and/or hydrolysed protein. In some cases, compositions in which a proportion of the amino acid content is provided by polypeptides or proteins are found to have a better taste than compositions with a high proportion of total amino acids provided as free amino acids and/or certain hydrolysed proteins. The availability of such compositions has been limited, however, because nutritional formulations have traditionally been made from protein isolated from natural food products, such as whey isolated from milk, or soy protein isolated from soy. The amino acid profiles of those proteins do not necessarily meet the amino acid requirements for a mammal. In addition, commodity proteins typically consist of mixtures of proteins and/or protein hydrolysates which can vary in their protein composition, thus leading to unpredictability regarding their nutritional value. Moreover, the limited number of sources of such proteins with a high biological value has meant that only certain combinations of amino acids are available on a large scale for ingestion in protein form.

The glycomacropeptide (GMP), a natural whey protein produced during cheese making, has been used in the treatment of PKU. GMP in its pure form lacks the aromatic amino acids phenylalanine (Phe; F), tyrosine (Tyr; Y) and tryptophan (Trp; W) as well as arginine (Arg; R), histidine (His; H) and cysteine (Cys; C) but is enriched in the large neutral amino acids isoleucine (Ile; I) and threonine (Thr; T). As a commercially available dietary protein it contains minimal amounts of Phe. However, used as single protein source in medical foods for the dietary management of PKU it has to be supplemented with Trp, Arg, Leu, His and Tyr to meet the needs of daily-required intake of these essential and semi-essential amino acids and to provide an adequate low Phe/Tyr ratio (<1). Becoming essential in PKU patients, Tyr improves their emotional behaviour dependent on the availability for the synthesis of neurotransmitters.

The present invention addresses the above issues by providing a dietary protein comprising all essential amino acids (expect Phe) that has improved properties, such as a high biological value or neutral taste. Moreover, the dietary protein may be provided as a nutritive product which can form a part of the patients' normal diet, such as baked goods, cereals or pressed bars. Alternatively, the dietary protein may be provided in a form that is suitable for the production of a nutritive product by the patient, such as pre-prepared baking mixtures or vegetable soup mixtures.

The present invention therefore aims at improving the quality of life of PKU patients, since all PKU patients must adhere to a special diet low in Phe for optimal brain development. "Diet for life" has become the standard recommended by most experts. The diet requires severely restricting or eliminating foods high in Phe, such as meat, chicken, fish, eggs, nuts, cheese, legumes, milk and other dairy products. Starchy foods, such as potatoes, bread, pasta and corn, must be monitored. The sweetener aspartame, present in many diet foods and soft drinks, must also be avoided, as aspartame consists of two amino acids: phenylalanine and aspartic acid.

Infants may still be breastfed to provide all of the benefits of breastmilk, but the quantity must also be monitored and supplementation for missing nutrients will be required. Supplementary infant formulas are used in these patients to provide the amino acids and other necessary nutrients that would otherwise be lacking in a low-phenylalanine diet. As the child grows up these can be replaced with tablets, formulas and specially formulated foods. Since Phe is necessary for the synthesis of many proteins, it is required for appropriate growth, but levels must be strictly controlled in PKU patients. In addition, tyrosine, which is normally derived from phenylalanine, must be supplemented in the diet of PKU patients.

The oral administration of tetrahydrobiopterin (or BH4) (a co-factor for the oxidation of phenylalanine) can reduce blood levels of Phe in certain patients. A tablet preparation of the compound sapropterin dihydrochloride (Kuvan®), which is a form of tetrahydrobiopterin, is commercially available. Kuvan® is the first drug that can help BH4-responsive PKU patients (ORPHA293284, depending on the clinical setting defined among clinicians as about 25-50% of the PKU population) lower Phe levels to recommended ranges. Working closely with a dietitian, some PKU patients who respond to Kuvan® may be able to increase the amount of natural protein they can eat. However, patients will still require a Phe-restricted diet.

In theory, synthetic polypeptide sequences comprising a desired mixture of amino acids could be designed and produced in a laboratory setting. This approach may raise various concerns, however, and is therefore not always applicable. First, skilled artisans are aware that obtaining high levels of production of such synthetic sequences may be very challenging. Second, even if such a synthetic protein were synthesized, its suitability for use in a nutritive product would be uncertain. For example, such a non-naturally occurring polypeptide could be an allergen or a toxin. Thus, natural proteins are preferred.

The replacement of Phe residues in natural proteins followed by recombinant production of those proteins has also been proposed in U.S. Pat. No. 6,495,344, relating to ovalbumin and casein, two highly abundant proteins in eggs and milk, respectively, and U.S. Pat. No. 6,004,930, which discloses gamma zeins, a class of proteins present in maize. However, replacing Phe in natural proteins is not always possible and may change the protein structure such that the protein is no longer expressed.

WO 2013/148332 relates to naturally occurring nutritive polypeptide sequences composed of combinations of amino acids that contain no Phe or low Phe, some of which are secreted. WO 2014/081884 relates to formulations of such isolated nutritive polypeptides, for example for nutritional purposes. WO 2016/046234 relates to a method for preparing a recombinant Phe-free or Phe-low protein.

SUMMARY OF THE INVENTION

It is an object of the invention to provide a recombinant Phe-free dietary protein with a high biological value for use in dietary compositions for patients with accumulation of phenylalanine in the body to provide all other essential amino acids in a dietarily sufficient balance.

In one aspect, the invention relates to a recombinant dietary protein comprising a polypeptide sequence that is at least 70% identical to SEQ ID NO 2. In one embodiment, the recombinant dietary protein comprises a polypeptide sequence that is at least 75%, more preferably at least 80%, more preferably at least 85%, more preferably at least 90%, more preferably at least 95%, more preferably at least 98% identical to SEQ ID NO 2. In an even more preferred embodiment, the recombinant dietary protein comprises a polypeptide sequence that is 100% identical to SEQ ID NO 2. The recombinant dietary protein may be a dietarily sufficient portion of the sequence of SEQ ID NO 2 that is with increasing preference at least 70%, 75%, 80%, 85%, 90%, 95%, 96%, 97%, 98% or 99% identical to SEQ ID NO 2.

In another embodiment, the recombinant dietary protein or dietarily sufficient portion thereof comprises one or more additional protein sequences that are purification tags or label. In a preferred embodiment, the additional protein sequence comprises SEQ ID NO 3.

In another aspect, the invention relates to a vector comprising a nucleic acid sequence encoding the recombinant dietary protein or dietarily sufficient portion thereof.

In another aspect, the invention relates to a recombinant microorganism comprising the vector encoding the recombinant dietary protein or dietarily sufficient portion thereof. In one embodiment, the microorganism is selected from the group consisting of *Escherichia, Klebsiella, Pseudomonas, Xanthomonas, Bacillus, Staphylococcus, Saccharomyces, Corynebacterium, Streptomyces, Salmonella, Aspergillus, Gluconobacter, Mycobacterium, Actinomycetes, Caulobacter, Pichia, Corynebacterium glutamicum, Saccharomyces cerevisiae, Clostridium botulinum, Flavobacterium heparinum, Lactococcus lactis, Methylobacterium extorquens, Pseudoalteromonas haloplanktis, Ralstonia eutropha, Neurospora crassa, Arxula adeninivorans, Hansenula polymorphs, Kluyveromyces lactis, Zygosaccharomyves bailii, Pseudomonas fluorescens, Bacillus subtilis* and *Bacillus megaterium*. In a preferred embodiment, the microorganism is selected from the group consisting of *Bacillus* or *Pseudomonas*. In a more preferred embodiment, said microorganism is *Bacillus subtilis* or *Pseudomonas fluorescens*.

In another aspect, the invention relates to a method of producing the dietary protein or dietarily sufficient portion thereof, the method comprising culturing the recombinant microorganism carrying the vector encoding the recombinant protein or dietarily sufficient portion thereof under suitable conditions for production. The recombinant dietary protein or dietarily sufficient portion thereof may be purified. In one embodiment, the purification is performed with the help of a purification tag. It is preferred that the purified recombinant protein or dietarily sufficient portion thereof comprises no more than 1 g Phe per 100 g protein, preferably no more than 0.45 g Phe contaminant per 100 g protein, more preferably no more than 0.35 g Phe contaminant per 100 g protein, more preferably no more than 0.25 g Phe contaminant per 100 g protein, more preferably no more than 0.15 g Phe contaminant per 100 g protein, more preferably no more than 0.13 g Phe contaminant per 100 g protein and most preferred no more than 0.10 g of Phe contaminant per 100 g protein.

In another aspect, the invention relates to a dietary composition comprising the dietary protein or dietarily sufficient portion thereof. In one embodiment the dietary composition consists of the dietary protein or a dietarily sufficient portion thereof. In another embodiment the dietary protein or a dietarily sufficient portion thereof is combined with further excipients. In a preferred embodiment, the dietary composition contains no more than 0.2 g of Phe per 100 g protein, preferably no more than 0.1 g of Phe contaminant per 100 g protein, more preferably no more than 0.05 g of Phe contaminant per 100 g protein, more preferably no more than 0.04 g of Phe contaminant per 100 g protein, more preferably no more than 0.03 g of Phe contaminant per 100 g protein and most preferred no more than 0.02 g of Phe contaminant per 100 g protein.

The dietary protein or dietarily sufficient portion thereof or the dietary composition is for use as food for special medical purposes; reference is made to the EU directives 2009/39/EG ("Diätrahmenrichtlinie") and 1999/21/EG ("diätetische Lebensmittel für besondere medizinische Zwecke") as well as to the EU regulation EU 609/2013 ("Food for special groups"; "Lebensmittel für Säuglinge und Kleinkinder, Lebensmittel für besondere medizinische Zwecke und Tagesrationen für gewichtskontrollierende Ernährung"), which will enter into force on Jul. 20, 2016. In particular, the dietary protein or dietarily sufficient portion thereof or said dietary composition may be for use in the management of a disorder characterized by accumulation of phenylalanine in the body, such as hyperphenylalaninemia (HPA), preferably phenylketonuria (PKU). Thus, in another aspect, the dietary protein or dietarily sufficient portion thereof or said dietary composition is for use as a medicament. In a preferred embodiment, the dietary protein or dietarily sufficient portion thereof is for use in the treatment of a disorder characterized by accumulation of phenylalanine in the body. In a more preferred embodiment, the disorder is HPA, more preferably PKU.

FIGURES

FIG. 1 shows the weight progression of PKU mice treated with standard mouse diet (group 1, no treatment), the Phe-free GSP105 protein diet (group 2) or the Phe-free amino acid diet (group 3, standard treatment) over 28 days of feeding. The x-axis marks days of the feeding period, the y-axis marks weight of the animals in grams.

FIG. 2 plots mean concentrations of Phe in the blood plasma of the three different mice groups over 28 days of feeding. The x-axis marks days of the feeding period, the y-axis marks the L-Phe level in micromoles per litre of blood plasma.

DETAILED DESCRIPTION

Figure 1:
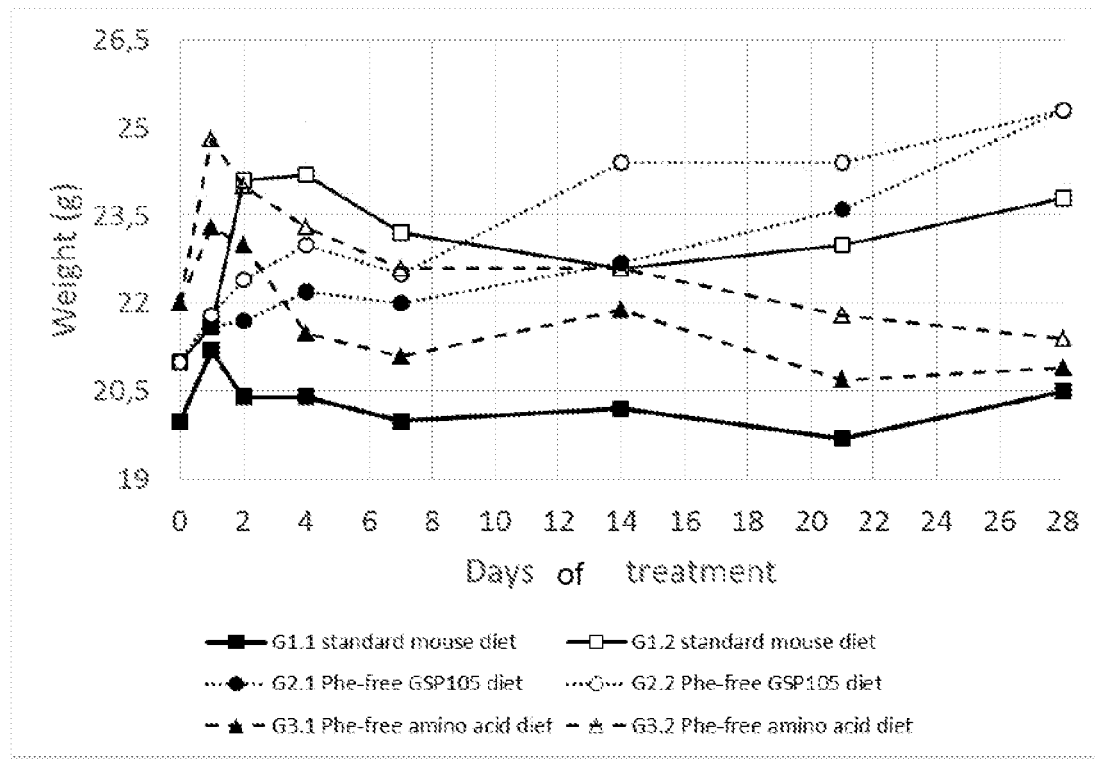

As used herein, "recombinant" refers to a biomolecule, e.g., a gene or protein, that (1) has been removed from its naturally occurring environment, (2) is not associated with all or a portion of a polynucleotide in which the gene is found in nature, (3) is operatively linked to a polynucleotide which it is not linked to in nature, and/or (4) does not occur in nature. The term "recombinant" can be used in reference to cloned DNA isolates, chemically synthesized polynucleotide analogues, or polynucleotide analogues that are biologically synthesized by heterologous systems, as well as proteins and/or mRNAs encoded by such nucleic acids. Thus, for example, a protein synthesized by a microorganism is recombinant if it is synthesized from an mRNA synthesized from a recombinant gene present in the cell.

The term "dietary protein", as used herein, refers to a protein suitable for human ingestion. Dietary proteins that provide all the essential amino acids are referred to as proteins with a high biological value. A Phe-free protein providing all other essential amino acids is also considered to be a protein with a high biological value. Casein (a protein commonly found in mammalian milk, making up 80% of the proteins in cow milk) and whey (the protein in the liquid that remains after milk has been curdled and strained) are major sources of dietary proteins with a high biological value. The dietary protein of the invention comprises all essential amino acids with the exception of Phe. The term "dietarily sufficient portion thereof" refers to a part of the dietary protein. The dietarily sufficient portion of the dietary protein has less amino acids than the dietary protein of the invention but still comprises all essential amino acids with the exception of Phe.

The term "dietarily sufficient", as used herein, refers to a polypeptide sequence that comprises all essential amino acids except phenylalanine and is a protein with a high biological value.

The term "essential amino acids", as used herein, refers to histidine (His, H), arginine (Arg, R), isoleucine (Ile, I), leucine (Leu, L), lysine (Lys, K), methionine (Met, M), phenylalanine (Phe, F), threonine (Thr, T), tryptophan (Trp, W) and valine (Val, V), which are amino acids necessary for health and growth, but which cannot be synthesized by the human body and must be obtained from food.

The term "recombinant microorganism", as used herein, refers to a microorganism that has been modified to carry a copy of a recombinant gene.

As used herein, a "dietary composition" is a composition suitable for human consumption. The dietary composition may comprise mostly protein. The dietary composition of the invention comprises the recombinant dietary protein of the invention or a dietarily sufficient portion thereof and is low in total phenylalanine.

The term "naturally occurring protein", as used herein, refers to a protein that is generated from a sequence unaltered by man present in a natural host. Therefore, neither the DNA sequence encoding the protein, nor the amino acid sequence of the protein itself, has been altered from the sequences found in the natural host.

For the purposes of this disclosure, a "nutritive product" is a product suitable for human consumption that comprises the recombinant dietary protein of the invention or a dietarily sufficient portion thereof or the dietary composition of the invention and contains a desirable amount of essential amino acids. The desirable amount of essential amino acids required for a patient per day depends on the age of the patient and diet of the patient, i.e. the level of protein- and/or Phe-restriction. The daily desirable amount can be determined by the physician and/or dietitian by known methods in the art. A typical amount is e.g. based on 0.8 g protein per kg body weight per day for adults or 1.2 g protein per kg body weight per day for children. The nutritive product itself, i.e. before the recombinant dietary protein of the invention or a dietarily sufficient portion thereof or the dietary composition of the invention is added, contains no protein or low protein components.

As used herein, a "purification tag" is any polypeptide that has a binding partner that can be used to detect, isolate and/or purify a second protein or polypeptide sequence of interest fused to the purification tag. Several examples are well known in the art and include a His-6 tag, a FLAG epitope, a c-myc epitope, a Strep-TAGII, a biotin tag, a glutathione 5-transferase (GST), a chitin binding protein (CBP), a maltose binding protein (MBP), a metal affinity tag or the Tag54 (Rasche et al., The Open Biotechnology Journal 2011, 5:1-6) or modifications thereof.

The invention relates in one aspect to a recombinant Phe-free dietary protein with a high biological value. Example 1 describes the process for identifying such a dietary protein used for the production of the recombinant Phe-free dietary protein of the invention that can be used for dietary management of patients with accumulation of phenylalanine in the body. The "general stress protein 16O (G16O_BACSU)" (SEQ ID NO 1) (protein data bank UniprotKb accession no. P80872) from *Bacillus subtilis* (strain 168) was identified as suitable protein candidate. The single Phe residue was replaced by the structurally similar amino acid tryptophan (Trp) by replacing the Phe coding base triplet with a tryptophan coding base triplet on cDNA level. This replacement results in a dietary protein containing no Phe but instead the essential amino acid Trp, thereby providing a dietary protein that contains all essential amino acids except Phe. The substitution is therefore advantageous for two reasons: first a Phe-free dietary protein is provided, second all other essential amino acids are present in the dietary protein and no supplementation is required. This is particularly advantageous, since Trp tastes very bitter and adding free Trp to a dietary composition would result in a bitter flavour. Moreover, it was surprisingly found that introducing the bitter tasting amino acid Trp did not result in a bitter tasting dietary protein. Thus, in one embodiment, the recombinant dietary protein with a high biological value which is Phe free and contains all essential amino acids has a polypeptide sequence that is identical to SEQ ID NO 2. Such a dietary protein is termed GSP105. In another embodiment, the recombinant dietary protein comprises a polypeptide sequence that is at least 70% identical to SEQ ID NO 2. More preferably, the recombinant dietary protein comprises a polypeptide sequence that is at least 75%, more preferably at least 80%, more preferably at least 85%, more preferably at least 90%, more preferably at least 95%, more preferably at least 98% identical, more preferably at least 99% identical and most preferred at least 100% identical to SEQ ID NO 2. It is to be understood that the sequence identity is to be determined with respect to sequence SEQ ID NO 2 over its entire length. For example, a protein comprising the sequence of SEQ ID NO 2 and having C- and/or N-terminal of the dietary protein further amino acids is considered to have a sequence identity of 100% to sequence SEQ ID NO 2, since the C- and/or N-terminal amino acids can be disregarded for the sequence comparison.

The recombinant dietary protein may comprise a dietarily sufficient portion of the sequence of SEQ ID NO 2 that is with increasing preference at least 70%, 75%, 80%, 85%, 90%, 95%, 96%, 97%, 98% or 99% identical to SEQ ID NO 2.

The recombinant dietary protein or dietarily sufficient portion thereof can comprise one or more additional protein sequences that are purification tags or label. The additional protein sequence can optionally be removed by cleavage. If the dietary protein or dietarily sufficient portion thereof comprises more than one additional protein sequence, each one, any combination or all can be removed by cleavage. It is to be understood that the additional protein sequence does not introduce a Phe residue, or, in cases where an additional protein sequence comprises a Phe residue, such additional protein sequence is removed by cleavage. In one embodiment, the additional protein sequence comprises SEQ ID NO 3. In a preferred embodiment, the additional protein sequence comprises a modified TAG54 (Rasche et al.) in which the Phe residue was replaced with another amino acid, preferably a tyrosine or alanine residue. Thus, in a particular preferred embodiment, the additional protein sequence comprises SEQ ID NO 4, the modified Tag54 in which the Phe residue was replaced with an alanine residue. In another particular preferred embodiment, the additional protein sequence comprises the modified Tag54 in which the Phe residue was replaced with a tyrosine residue (SEQ ID NO 5). Such a replacement has the advantage that the Tyr content is increased and the Phe/Tyr ratio of the dietary protein is decreased. In a further preferred embodiment, the recombinant dietary protein or dietarily sufficient portion thereof comprises additionally a C-terminal His-6 tag. In a particularly preferred embodiment, the recombinant dietary protein comprises a polypeptide sequence that is identical to SEQ ID NO 2 and comprises as additional protein sequences a C-terminal His-6 tag and SEQ ID NO 4, resulting in the tagged recombinant dietary protein having the sequence disclosed in SEQ ID NO 6 (=GSP105-6His-Tag54-P15). The characteristics of the tagged recombinant dietary protein (SEQ ID NO 6) compared to the general stress protein 16O (GSP16O) of *B. subtilis* are listed in Table 1.

TABLE 1

Comparison of naturally occurring protein GSP16O and the tagged recombinant dietary protein GSP105 (SEQ ID NO 6) produced in *Bacillus subtilis* and *Pseudomonas fluorescens*

|  | GSP16O | GSP105-6His-Tag54-P15 | |
| --- | --- | --- | --- |
| Origin | *B. subtilis* | *B. subtilis* | *Pseudomonas fluorescens* |
| Phe content [%] | 0.6 | 0 | 0 |
| molecular weight [kDa] | 19 | 21 | 21 |
| modifications | — | Phe → Trp His6 tag, Tag54-P15 | Phe → Trp His6 tag, Tag54-P15 |
| special properties | secreted, heat stable | secreted, heat stable, neutral flavour | heat stable, neutral flavour |

The His-6 tag and/or modified Tag54 can be used for purification of the recombinant dietary protein or a dietary sufficient portion thereof. It was surprisingly found that the Tag54-P15 tag improves the expression of the protein in *B. subtilis*. Further, the additional protein sequence of the modified Tag54 advantageously provides amino acids for the total amino acid composition of the dietary protein thereby improving the total amino acid composition of the recombinant dietary protein. Further still, the modified Tag54 can serve as a detection epitope for the fusion protein.

The recombinant dietary protein of the invention or a dietarily sufficient portion thereof may further comprise a designer tail. A "designer tail" refers to a short stretch of amino acids that can be added to the C- or N-terminus of the protein. The designer tail contains 1 to 5 amino acids. In one embodiment, the dietary protein comprises a polypeptide sequence that is at least 70% identical to SEQ ID NO 2 and a designer tail. Optionally, the dietary protein may further comprise one or more additional protein sequences, such as a His-6 tag and/or a modified Tag54. In a preferred embodiment, the designer tail is made of tyrosine. In a particularly preferred embodiment, the designer tail has one tyrosine, more preferably two tyrosines and most preferred three tyrosines. Thus, in one embodiment, the dietary protein or a dietarily sufficient portion thereof comprises a polypeptide sequence that is at least 70% identical to SEQ ID NO 2, a designer tail made of tyrosine comprising at least one tyrosine residue, a His-6 tag and a modified Tag54.

In another aspect, the invention relates to a vector comprising a nucleic acid sequence encoding the recombinant dietary protein of the invention or a dietarily sufficient portion thereof. In one embodiment, the vector is a plasmid. In a preferred embodiment, the plasmid is the IPTG-inducible expression plasmid pHT43 (MoBiTec) or the IPTG-inducible expression plasmid pDAB107209 (Dow; US2008/0269070 A1).

A nucleic acid sequence encoding the recombinant dietary protein of the invention or a dietarily sufficient portion thereof can readily be determined by a person skilled in the art using known methods such as reverse translation. Reverse translation is a method where a protein sequence is used as input and after using a codon usage table a DNA sequence representing the most likely non-degenerate coding sequence is obtained. The obtained nucleic acid sequence can be optimized by using known optimization algorithms. This enabled the skilled person to obtain a nucleic acid sequence optimized for the expression in a specific host. The skilled person can also obtain nucleic acids commercially by providing the desired amino acids sequence and host organism in which the protein is to be produced. An exemplary nucleic acid sequence for the production of the recombinant dietary protein having the polypeptide sequence of SEQ ID NO 6 in *B. subtilis* is shown in SEQ ID NO 7. It is however to be understood that other nucleic acid sequences, such as nucleic acid sequences being codon optimized for specific host cells, may deviate from the exemplary sequence while still producing the recombinant dietary protein of the invention or a dietarily sufficient portion thereof. Even for the same organism nucleic acid sequence may vary depending on the commercial producer and the algorithm used.

In another aspect, the invention relates to a recombinant microorganism comprising the vector that comprises a nucleic acid sequence encoding the recombinant dietary protein of the invention or a dietarily sufficient portion thereof. Thus, the invention relates to a recombinant microorganism expressing the recombinant dietary protein of the invention or a dietarily sufficient portion thereof. In one embodiment, the microorganism is selected from the group consisting of *Escherichia*, *Klebsiella*, *Pseudomonas*, *Xanthomonas*, *Bacillus*, *Staphylococcus*, *Saccharomyces*, *Corynebacterium*, *Streptomyces*, *Salmonella*, *Aspergillus*, *Gluconobacter*, *Mycobacterium*, *Actinomycetes*, *Caulobacter*, *Pichia*, *Corynebacterium glutamicum*, *Saccharomyces cerevisiae*, *Clostridium botulinum*, *Flavobacterium heparinum*, *Lactococcus lactis*, *Methylobacterium extorquens*, *Pseudoalteromonas haloplanktis*, *Ralstonia eutropha*, *Neurospora crassa*, *Arxula adeninivorans*, *Hansenula polymorphs*, *Kluyveromyces lactis*, *Zygosaccharomyces bailii*, *Pseudomonas fluorescens*, *Bacillus subtilis* and *Bacillus megaterium*. In a preferred embodiment, the microorganism is selected from the group consisting of *Bacillus* or *Pseudomonas*. In a more preferred embodiment, the microorganism is *Bacillus subtilis* or *Pseudomonas fluorescens*.

In another aspect, the invention relates to a method of producing the recombinant dietary protein of the invention or a dietarily sufficient portion thereof, the method comprising culturing the recombinant microorganism of the invention under conditions suitable for production of the dietary protein or dietarily sufficient portion thereof by the recombinant microorganism. In one embodiment, the method comprises cultivating the recombinant microorganism, extracting the recombinant dietary protein or dietarily sufficient portion thereof, purifying the recombinant dietary protein or dietarily sufficient portion thereof and drying the obtained protein. In another embodiment, the method comprises the steps of cultivating the recombinant microorganism, such as *Bacillus*, harvesting the supernatant, optionally concentrating the supernatant, purifying the recombinant dietary protein or dietarily sufficient portion thereof, exchanging the buffer to water and freeze and/or spray and/or drum and/or extrusion drying the obtained protein. The cultivation of the recombinant microorganism preferably comprises the use of starter and main cultures. The harvesting and concentration of the supernatant preferably comprises diafiltration, more preferably cross-flow filtration using hollow fibres having different pore sizes. It is preferred that the supernatant after concentration is concentrated at least 10-fold. Purification of the recombinant dietary protein or dietarily sufficient portion thereof may comprise immobilized metal ion affinity chromatography (IMAC), preferably using zinc ions and chelating sepharose. Optionally the purified protein can be concentrated after exchanging the buffer to water. Thus, in a preferred embodiment, the method comprises the steps of cultivating the recombinant microorganism using starter and main cultures, harvesting the supernatant, concentrating the supernatant at least 10-fold, purifying the recombinant dietary protein or dietarily sufficient portion thereof, exchanging the buffer to water, optionally concentrating the purified protein, and freeze and/or spray drying the obtained protein.

The method of producing the recombinant dietary protein of the invention or a dietarily sufficient portion thereof results in high protein yields, such as at least 100-500 mg/L in *B. subtilis* or at least 2.4 g/L in *Pseudomonas fluorescens*. The purified recombinant protein or dietarily sufficient portion thereof comprises no more than 1 g Phe per 100 g protein, preferably no more than 0.45 g Phe contaminant per 100 g protein, more preferably no more than 0.35 g Phe contaminant per 100 g protein, more preferably no more than 0.25 g Phe contaminant per 100 g protein, more preferably no more than 0.15 g Phe contaminant per 100 g protein, more preferably no more than 0.13 g Phe contaminant per 100 g protein and most preferred no more than 0.10 g of Phe contaminant per 100 g protein.

The purified freeze and/or spray and/or drum and/or extrusion dried protein can be stored in a frozen state, such as at −20° C., under cooled conditions, such as at 4° C., or at room temperature. In a preferred embodiment, the purified freeze and/or spray and/or drum and/or extrusion dried protein is stored at −20° C.

In another aspect, the invention relates to a dietary composition comprising the recombinant dietary protein of the invention or a dietarily sufficient portion thereof, either alone or optionally with further excipients. In one embodiment, the dietary composition of the invention is supplemented with additional excipients selected from the group consisting of essential vitamins, minerals and trace elements, vitamin-like substances (such as, but not limited to taurine, myo-inositol, choline and carnitine), lipids (such as, but not limited to, fats, oils, fatty acids, docosahexaenoic acid (DHA), eicosapentaenoic acid (EPA), triglycerides, phospholipids, lecithin, fatty acid esters or cholesterol), carbohydrates (such as, but not limited to, mono-/di-/oligo-/polysaccharides, starch, glucans, fructans or pentosans), nucleotides, protein, peptides, amino acids (such as tyrosine) and reaction products thereof, acids, acidity regulators, anti-caking agents, anti-foaming agents, anti-oxidants, binders, buffers (such as, but not limited to, sodium citrate, magnesium carbonate, magnesium bicarbonate, calcium carbonate, calcium bicarbonate), bulking agents, emulsifiers, enzymes, firming agents, flavours, flavour enhancers, foaming agents, gelling agents (such as, but not limited to, guar, xanthan, alginate, carrageen, pectin), glazing agents, humectants, modified starches, preservatives, propelling gas, raising agents, sequestrants, stabilizers, thickeners (such as, but not limited to, starch, cellulose), sweeteners, food colours, herbs, spices, plant extracts and phytochemicals. In a preferred embodiment the dietary composition may be supplemented with tyrosine.

In one embodiment the dietary composition is prepared as powder, granules, tablet, capsule, agglomerate, frozen composition, pellet, solution, macromolecular solution, hydrocolloid, complex disperse system, suspension, emulsion, liquid, foam, gel, sol, solid sol, solid foam, crystal, amorphous solid, pill, extrudate or paste. The dietary composition can be stored with or without cooling in a dried, freeze dried, spray dried, drum dried or extrusion dried form.

In a preferred embodiment, the dietary composition contains no more than 0.2 g of Phe per 100 g protein, preferably no more than 0.1 g of Phe contaminant per 100 g protein, more preferably no more than 0.05 g of Phe contaminant per 100 g protein, more preferably no more than 0.04 g of Phe contaminant per 100 g protein, more preferred no more than 0.03 g of Phe contaminant per 100 g protein and most preferred no more than 0.02 g of Phe contaminant per 100 g protein.

The recombinant dietary protein of the invention or a dietarily sufficient portion thereof or the dietary composition of the invention may be used in a nutritive product. The nutritive product can be selected from, but is not limited to, the group consisting of drinks, soups, pressed bars, wafers, waffles, puddings, gel-like foods, meat-like foods such as meat analogues comprising non-animal fibres, sausage analogues, baked goods, sauces, salad dressings, cereals, flakes, baking mixes, such as muffin mixes, waffle mixes or crêpes mixes, meals, cookies, crackers, crèmes, mousses, flans, custards, compotes, ice cream, sorbets, parfaits, dips, spreads, syrups, purées, paste, jellies, butters, jams, cheese analogues, cream cheese analogues, yoghurt analogues, milk analogues, crisps and extruded solids. The nutritive product can be produced and bought comprising the dietary composition of the invention or prepared individually by the patient. For example, drinks or soups may be prepared by adding the dietary composition to water, fruit juice, rice milk or vegetable broth. Advantageously, the recombinant dietary protein or dietarily sufficient portion thereof tolerates heat treatments without changes in its nutritional value, consistency or flavour. Thus, when preparing a nutritive product, such as e.g. baked goods, cereals, soups or pressed bars, the recombinant dietary protein or a dietarily sufficient portion thereof may be heated, baked, boiled, fried, deep fried, sautéed, stewed, braised, roasted, steamed, poached, simmered, grilled, sous-vide cooked, homogenized, sterilized, tyndallized, high pressure-low temperature treated, vacuum cooked, freeze processed, pasteurized or extruded.

In one embodiment, the nutritive product contains very low amounts of Phe. In a preferred embodiment, the nutritive product contains no Phe. The amount of Phe contaminant in the dietary composition of the invention that is added to the nutritive product can vary depending on the nutritive product. In one embodiment, the nutritive product contains no more than 0.2 g of Phe per 100 g protein, preferably no more than 0.1 g of Phe contaminant per 100 g protein, more preferably no more than 0.05 g of Phe contaminant per 100 g protein, more preferably no more than 0.04 g of Phe contaminant per 100 g protein, more preferred no more than 0.03 g of Phe contaminant per 100 g protein and most preferred no more than 0.02 g of Phe contaminant per 100 g protein.

In another aspect, the invention relates to the recombinant dietary protein of the invention or a dietarily sufficient portion thereof or the dietary composition of the invention for use as a medicament and/or food for special medical purposes. The recombinant dietary protein or a dietarily sufficient portion thereof or the dietary composition can be in the form of a powder, granules, tablet, pellet, suspension, emulsion, liquid, pill, extrudate or paste. The administration can be three to five times a day. The dosage can e.g. be at least 5, 10, 15, 20, 30, 40 or 50 g dietary protein. The administration can be with meals. The administration can be orally or enterally. Preferably, the administration is orally. The medicament can be administered to children, teenagers and adults. In a preferred embodiment, the recombinant dietary protein of the invention or a dietarily sufficient portion thereof or the dietary composition of the invention is for use in the treatment of a disorder characterized by accumulation of phenylalanine in the body. In an even more preferred embodiment, the disorder is hyperphenylalaninemia or phenylketonuria.

In a further preferred embodiment, the recombinant dietary protein or a dietarily sufficient portion thereof or the dietary composition is used in combination with a medicament for the management of PKU or HPA, such as BH4 or analogous thereof.

The suitability of the recombinant dietary protein of the invention for use in the management of phenylketonuria (PKU) is shown in Example 3. Example 3 shows the results of a pilot study in which PKU mice are treated either with a diet in which their sole amino acid source is a free amino acid mixture without Phe but with 1.5% Tyr (Harlan Teklad TD.97152; Seagraves and McBride, Mol Genet Metab 2012, 107(4):650-658) (referred herein as "Phe-free amino acid diet") which resembles the current standard in medical foods for PKU patients, or with a diet in which their sole amino acid source is the recombinant dietary protein GSP105 supplemented with 0.2% Phe (referred herein as "Phe-free GSP105 protein diet" or "Phe-free GSP105 diet"). Supplementation of the diet with Phe in the experiment was done because the mice had otherwise no access to this essential amino acid. The mice fed with the Phe-free GSP105 protein diet showed weight maintenance or weight gain as opposed to the mice fed with the Phe-free amino acid diet which showed weight loss (FIG. 1). This may be explained by the fact that the recombinant dietary protein is a structurally intact protein source. While within the field of dietetics there is a debate on whether proteins and protein fragments remain available for metabolic purposes compared to compositions of free amino acids, it is believed that the pool of available amino acids from a crystalline amino acid composition has to be metabolized immediately, since the body cannot store them for future metabolic use. Proteins and protein fragments, however, are successively digested, which provides a continuous release of free amino acids available for metabolic purposes over a longer period of time. Thus, using the recombinant dietary protein of the invention or a dietary sufficient portion thereof or the dietary composition of the invention could provide amino acids over a longer period, thereby resulting in weight maintenance or weight gain.

Without being bound by theory, the weight loss in mice fed with the Phe-free amino acid diet could also derived from a lack of the minimum required Phe amount in the diet, since it is possible that the animals reached catabolic metabolism in which endogenous protein was metabolized to maintain the required Phe levels in the blood. Such a phenomenon can also be observed in PKU patients suffering from malnutrition, who metabolize endogenous protein and in turn suffer from elevated blood Phe levels. The complete and absolute absence of Phe in the diet of PKU patients is not desirable and impossible, thus PKU patients obtain the minimal amount of the essential amino acid Phe with their food. Malnutrition on the other hand can occur in PKU patients, since the strict diet can cause a lack in other essential amino acids as well. Thus, using the recombinant dietary protein of the invention or a dietary sufficient portion thereof or the dietary composition of the invention could prevent malnutrition in PKU patients.

EXAMPLES

Example 1—Candidate Gene Discovery

To identify potential protein candidates that meet the required criteria for a phenylalanine free nutritional protein, a self-designed search algorithm was used. Protein sequences from various genera or species were obtained from UniProt Database using the import feature of CLC Main Workbench 6.6.1.

Proteins originated from species which are common sources for food like vegetables (e.g. potato), but also originating from microorganisms (e.g. yeast) or animals (e.g. bovine) were used. Either the Latin or common name of the species/genus, depending which name resulted in the larger number of hits, was used as a search string. All hits except uncharacterized proteins were downloaded, resulting in a total number of 836,037 sequences from various species. The following search strings were used to identify the hits listed in Table 2.

The "Create Sequence Statistics" function within CLC with batches of 5,000 to 10,000 sequences were used further to generate lists of the amino acid present in each of the 836,037 genes. These lists were imported into Excel, were the amino acid composition was compared with two nutritional standards: the so called potato-egg principle (Kartoffel-Ei Standard, KES) as well as the amino acid composition the manufacturer Milupa is using in its PKU1 product, a Phe-free amino acid composition used for treatment of PKU patients.

Additionally, the total number of Phe in the amino acid sequence, as well as the total number of amino acids was analysed. All analysed factors were rated according to the settings in Table 3.

TABLE 2

Search strings for selection of genes and the corresponding hit number

| Search string | Hits |
| --- | --- |
| *Lactobacillus* | 259251 |
| *Bifidobacterium* | 80262 |
| *Saccharomyces cerevisiae* | 73620 |
| *Oryza* | 67411 |
| Maize | 63309 |
| *Bacillus subtilis* | 47456 |
| *Panicum* | 40273 |
| *Setaria* | 39691 |
| *Solanum lycoperison* | 37921 |
| *Sorghum* | 34201 |
| Barley | 26663 |
| *Salmo* | 14939 |
| *Tiriticum* | 8766 |
| *Bos taurus* | 7498 |
| *Citrus* | 5694 |
| *Sus scrofa* | 4905 |
| *Sebastes* | 2980 |
| Potato | 2548 |
| *Ipomoea* | 1635 |
| *Cyprinus* | 1559 |

TABLE 2-continued

Search strings for selection of genes
and the corresponding hit number

| Search string | Hits |
|---|---|
| Essox | 1509 |
| Porphyra | 1214 |
| Gadus | 1084 |
| Psetta | 979 |
| Musca | 898 |
| Strawberry | 739 |
| Secale | 721 |
| Carrot | 668 |
| Spinacia oleracea | 624 |
| Chickpea | 584 |
| Thunnus | 551 |
| Latuca sativa | 500 |
| Linum usitatissimum | 499 |
| Salvia | 472 |
| Cucurbita | 401 |
| Cucurbita | 395 |
| Pennisetrum | 374 |
| Crataegus | 289 |
| Eragrostis | 288 |
| Eleusine | 288 |
| Coix | 274 |
| Papalum | 245 |
| Mango | 241 |
| Merluccius | 231 |
| Clupea | 221 |
| Lophius | 163 |
| Echinochloa | 154 |
| Equisetum arvense | 146 |
| Urchloa | 145 |
| Wheat + storage | 112 |
| Digitaria | 101 |
| Hypericum perforatum | 84 |
| Achillea millefolium | 81 |
| Sardina | 76 |
| Pollachius | 60 |
| Plantago lanceolata | 57 |
| Verbascum | 45 |
| Thymus | 44 |
| Viscum album | 44 |
| Urtica dioica | 42 |
| Matricaria | 40 |
| Rosmarinus officinalis | 24 |
| Tussilago farfara | 18 |

Hits above a total score of 20 (sum of the scores for Phe content, molecular weight and deviation to KES and PKU1 of a single protein) were manually rated in terms of sequence status (complete or partial), protein existence (evidence at protein level, predicted, inferred from homology), protein function and allergenic potential. Proteins with a complete sequence, evidence at protein level and lacking allergenic potential were pre-selected and further analysed regarding their molecular function. All proteins having a known or predicted DNA/RNA binding activity as well as toxic proteins were rejected from the list of potential candidates.

Among the remaining candidates we identified the "General stress protein 16O (G16O_BACSU)" from Bacillus subtilis (strain 168) as suitable protein candidate.

Based on the protein sequence published at UniProt we designed a synthetic gene using the reverse translation function of CLC Main Workbench.

TABLE 3

Protein candidate assessment

| Phenylalanine content | | Molecular weight | | Deviation in amino acid composition in relation to PKU1 and KES (without F, Q, N) | |
|---|---|---|---|---|---|
| Total number of Phe | Score | AS | Score | Deviation | Score |
| >10 | −10 | >500 | 0 | >80 | −2 |
| <10 | 1 | <500 | 1 | <80 | 0 |
| <6 | 2 | <200 | 2 | <60 | 2 |
| <3 | 4 | <80 | 0 | <40 | 5 |
| <2 | 8 | <50 | −100 | <30 | 10 |
| <1 | 10 | | | | |

* Deviation is calculated as the added absolute value between each amino acid in the analysed protein sequence compared to the KES and PKU1 reference composition (percentaged).

Two epitope tag sequences (Tag54-P15, His6-tag) were added to the 3' end of the General stress protein (GSP) coding sequence to enable specific protein detection, quantification and purification resulting in the nucleotide sequence shown in SEQ ID NO 7. Additionally, BamHI and AatII restriction enzyme sites were added to the 5' and 3' end allowing the cloning of the gene construct into an expression vector.

The gene sequence was designated as GSP105 and optimized with respect to codon usage and RNA stability for expression in Bacillus subtilis and subsequently synthesized by GenScript (USA).

Example 2—Production in B. Subtilis

The synthetic gene GSP105 having the nucleotide sequence as shown in SEQ ID NO 7 was inserted into the Bacillus subtilis expression vector pHT43 (MoBiTec, Göttingen, Germany), enabling the secretion of the recombinant protein into the culture medium, and introduced into the protease deficient B. subtilis strain WB800N (MoBiTec), following the manufactures instructions.

After transformation, positive clones were selected on antibiotic selection plates; the presence of the expression vector was further confirmed by PCR, plasmid extraction and subsequent DNA sequencing. Glycerol stock cultures were generated and stored at −80° C.

A starter culture of the recombinant B. subtilis GSP105 was prepared by inoculating 1 L TB-medium (Carl Roth, Karlsruhe, Germany), supplemented with chloramphenicol (Carl Roth) and neomycin (Carl Roth) at final concentrations of 5 μg/ml each, with 1 ml B. subtilis GSP105 stock solution. The culture was grown for 24 h at 28° C. and 160 rpm in 2.5 L "Ultra Yield Flasks" (Thomson Instrument Company, California, USA).

For recombinant protein expression, TB-medium supplemented with chloramphenicol and neomycin was inoculated with the starter culture at a 1:20 (v/v) ratio. To induce the expression of the target protein, IPTG was added to a final concentration 0.5 μM. The culture was grown for 20 h at 37° C. and 160 rpm.

After cultivation cells were removed by centrifugation, followed by sterile filtration using a 0.22 μm hollow fibre filtration module (N02-E20U-05-N, Spectrum Labs, Los Angeles, USA) at 2.5 L/min with up to 1.6 bar transmembrane pressure. To reduce the process volume, the clarified culture supernatant was concentrated 10-fold using a 10 kDa hollow fibre module (N02-E010-05-N, Spectrum Lab) at 2.5 L/min with up to 1.6 bar transmembrane pressure.

GSP105 was purified from the concentrated culture supernatant via IMAC using 500 ml Chelating Sepharose (GE Healthcare, Uppsala, Sweden) packed into a XK 50/40 column and charged with Zn ions according to the manufactures instructions. The supernatant was loaded onto the column with 76 cm/h; afterwards the column was washed with 5 column volumes (CV) PBS at 92 cm/h. The bound protein was eluted from the column with 5 CV PBS, pH 8.0, 250 mM imidazole at 92 cm/h. IMAC elution fractions were pooled and the buffer was exchanged to salt-free water using a 10 kDa hollow fibre module (S02-Eo10-05N, Spectrum Labs) at 900 ml/min with up to 1.6 bar transmembrane pressure. To ensure efficient buffer exchange, the sample volume was replaced seven times. The purified and re-buffered protein was stored at −20° C. and subsequently freeze- and spray-dried.

The concentration of GSP105 was determined via competition ELISA (Piotrzkowski et al., PLoS ONE, 2012, 7(9):e45803), protein integrity and purity were confirmed by SDS-Gel and immunoblot (Rasche et al.).

Example 3—Mouse Feeding Study (Pilot Study)

Study Design:

Six adult, male, homozygous PKU mice (Pah$^{enu2/2}$; Shedlovsky et al., Genetics 1993, 134:1205; were separated into 3 groups of 2 mice each. Animals belonging to the same group shared a cage. The groups were fed diets as listed in Table 4. The main differences between diets were the protein component and the Phe content, as laid out in Table 5. Prior to the feeding study, the PKU mice were fed standard mouse diets. The feeding study extended over a period of 28 days, during which the animals were given food and water ad libitum.

TABLE 4

Animal groups and animal diets (N = 6)

| Animal group | Diet | Number of animals |
|---|---|---|
| 1 | Standard mouse diet | 2 |
| 2 | Phe-free GSP105 protein diet | 2 |
| 3 | Phe-free amino acid diet | 2 |

TABLE 5

Animal diets

| Diet | % protein | Phe content |
|---|---|---|
| Standard mouse diet | 18.5 (raw protein) | Raw protein (casein) |
| Phe-free GSP105 protein diet | 18.5 (GSP105) | GSP105, Phe supplemented at 2 g/kg |
| Phe-free amino acid diet (Harlan Teklad, TD.97152) | 15.4 (free amino acids) | Replaced with 1.5% tyrosine |

The "Phe-free GSP105 protein diet" or "Phe-free GSP105 diet" refers to a diet in which the sole amino acid source is the recombinant dietary protein GSP105 supplemented with 0.2% Phe. The Phe-free GSP105 protein diet was not entirely free of Phe. The purified GSP105 protein fraction contained a small amount of contamination likely resulting from trace media or secondary metabolites that amounted to 0.45 grams of Phe per 100 g of total protein. The GSP105 protein itself was completely Phe-free. The minor Phe contamination did not pose any problems for the PKU mice. Moreover, since Phe is an essential amino acid and no alternative nutritive sources were made available to the animals, crystalline Phe was added to the Phe-free GSP105 protein diet to a final Phe concentration of about 0.2%.

The "Phe-free amino acid diet" refers to a diet in which the sole amino acid source is a free amino acid mixture without Phe but with 1.5% Tyr which resembles the current standard in medical foods for PKU patients. The Phe-free amino acid diet was entirely free of Phe, while the tyrosine content was increased to 1.5%.

In the "standard mouse diet" the sole protein source was casein.

On days 0, 1, 7, 14, 21 and 28 5-10 µl of blood were sampled from the tail vein of the animals after they had fasted for 4 hours. The blood plasma Phe and tyrosine content was determined by MS/MS analysis.

On days 0, 1, 2, 4 and 7, the mice were weighed and their general health checked.

On days 14, 21 and 28, the mice were weighed only. On day 28, all animals were euthanized with $CO_2$. Liver, kidneys, brain and hearts of each animal was harvested and frozen in liquid nitrogen for further assays.

Results:

Body Weight

Feeding of the standard mouse diet resulted in principle in weight maintenance (FIG. 1, solid lines with squares). When fed the Phe-free GSP105 protein diet the PKU mice gained weight (FIG. 1, dotted lines with circles), while those mice fed the Phe-free amino acid diet demonstrated a slight weight loss (FIG. 1, disrupted lines with triangles). While small group size did not allow for statistical analysis, the observed trend supports GSP105 as a protein component suitable for weight maintenance and/or weight gain. The observed weight gain may be due to the fact that it is a dietary protein with a higher biological value than casein.

Reduction of Blood Phe Levels

Figure 2:
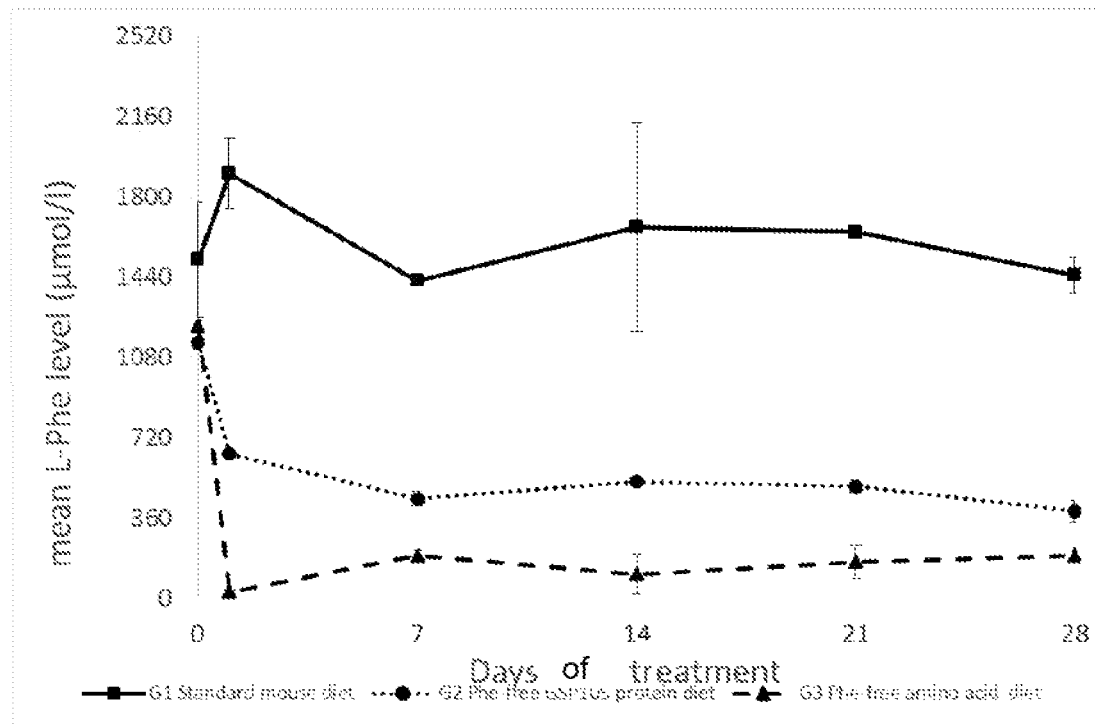

PKU mice on the standard mouse diet retained an elevated average Phe level in the blood (FIG. 2, solid line with squares). The Phe-free amino acid diet resulted in a drastic lowering of mean Phe levels in the blood (<360 micromoles per litre, the physiological range aimed for in PKU treatment) (FIG. 2, disrupted line with triangles). The mean blood Phe levels of animals on the Phe-free GSP105 protein diet also were clearly lowered, approaching <360 micromoles per litre after 28 days (FIG. 2, dotted line with circles). These results indicate that the disclosed recombinant dietary protein is suitable for dietary PKU management.

Figure 3:
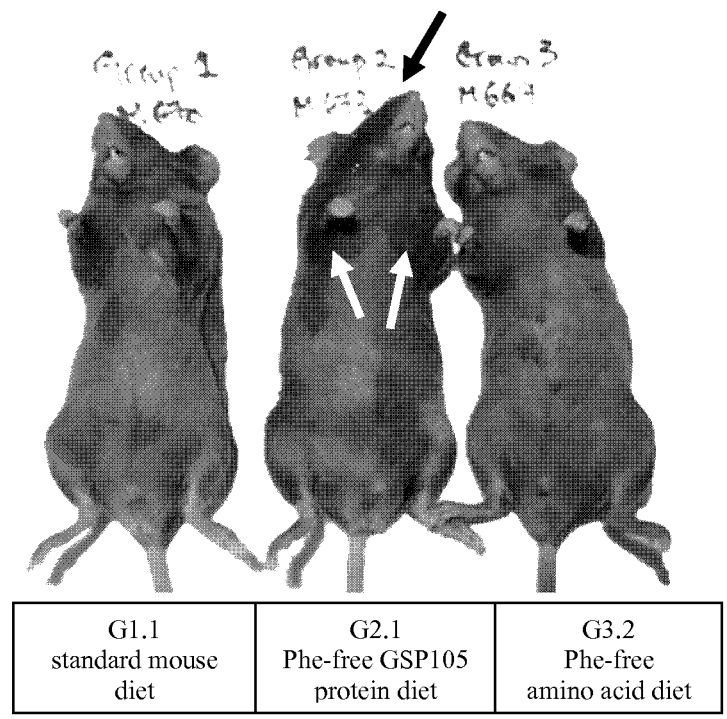
FIG. 3 shows an exemplary mouse of each diet group with differentially expressed, more or less partial changes in mouse coat hypopigmentation after 28 days of feeding.
Figure 3:
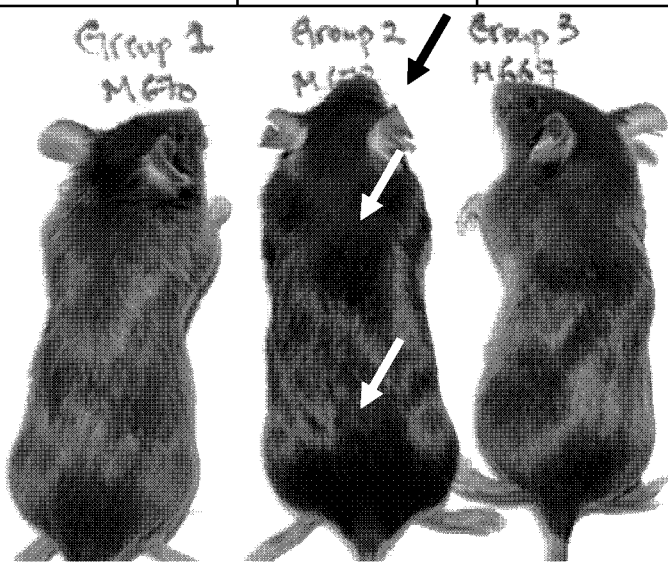

Untreated PKU mice with the genetic background C57BL/6 have brown fur as opposed the black fur observed in wild type mice of the same background, a phenomenon called hypopigmentation. Elevated blood Phe levels inhibit the enzyme tyrosinase, which disrupts synthesis of the pigment melanin. The lowered blood Phe levels of the mice fed diets free of or low in Phe resulted in a not fully complete but partial reversion of the hypopigmentation on the entire body in animals (FIG. 3). FIG. 3 shows an exemplary mouse of each diet group with differentially expressed, more or less partial changes in mouse coat hypopigmentation after 28 days of feeding. Each mouse is shown dorsally and ventrally. The mice fed with the Phe-free GSP105 protein diet showed a nearly complete black colour on the ventral side. The black and the white arrows indicate the strongest reversion of hypopigmentation reached after the feeding period. We assume a complete reversion of the fur colour from brown to black in case of diets free of or low in Phe with a prolonged feeding period.

Phe/Tyr Ratios in Blood Plasma

Figure 4:
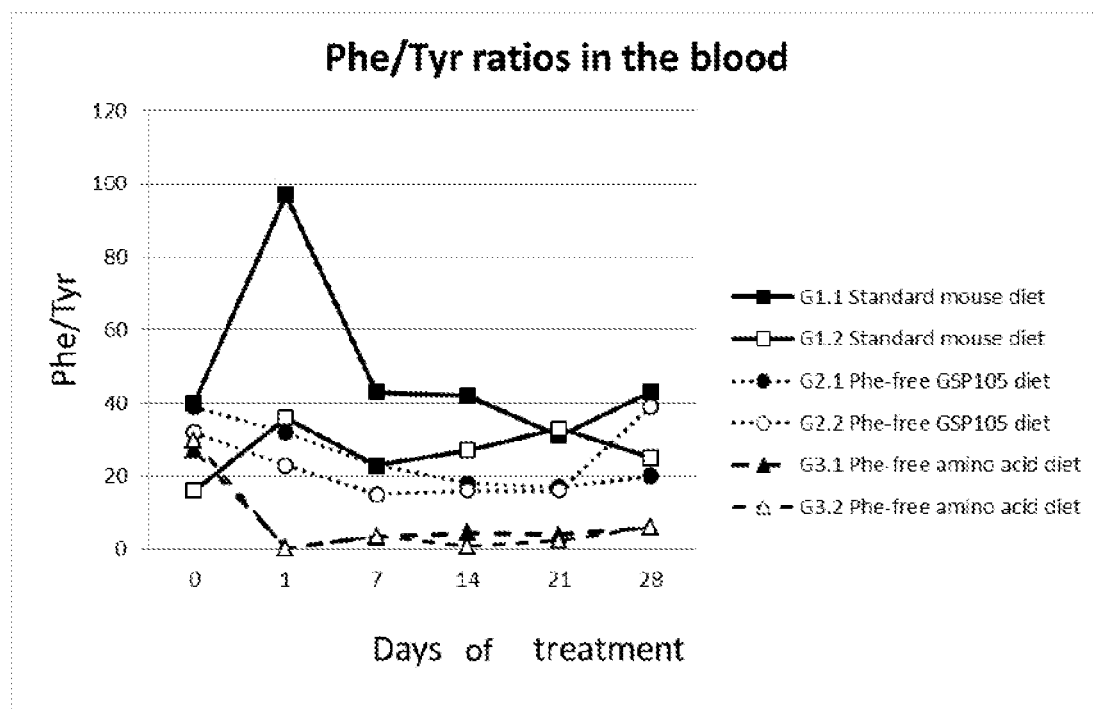
FIG. 4 shows the ratio of phenylalanine to tyrosine in the blood of the three different mice groups over 28 days of feeding. The x-axis marks days of the feeding period, the y-axis marks phenylalanine/tyrosine in the blood.

The Phe-free amino acid diet resulted in the lowest Phe/Tyr ratio in the blood plasma of PKU mice (FIG. 4, disrupted lines with triangles), followed by the Phe-free GSP105 protein diet (FIG. 4, dotted lines with circles). The PKU mice on the standard mouse diet mice are depicted in FIG. 4 as solid lines with squares as reference. The Phe/Tyr ratio for the Phe-free GSP105 protein diet could be improved by reducing the amount of Phe contaminant from the purified recombinant dietary protein GSP105, and/or by supplementation of crystalline tyrosine, as used in the Phe-free amino acid diet, or addition of a tyrosine containing designer tail.

Example 4—Measurement of Phe and Tyr Concentrations in the Brain of PKU Mice of Example 3

Methods:
Preparation of Mouse Brain Tissue

The brains of the animals of Example 3 were used. Whole frozen mouse brains were thawed on ice and lysed in homogenization buffer (10 μl/mg tissue) containing 50 mm Tris-HCl, pH 7.5, 0.1 m KCl, 1 mm EDTA, 1 mm dithiothreitol, 0.2 mm phenylmethylsulfonyl fluoride, 1 μm leupeptin and 1 μm pepstatin, and homogenized using Quiagen TissueLyser II at 4° C. After centrifugation at 13,000 g and 4° C. for 30 min, supernatants were kept frozen at −80° C.
Protein Measurement Protein concentrations in homogenized tissues were determined by the spectrophotometric method described by Bradford, using γ-globulin as a calibrator.
Sample Preparation and Derivatization Samples were prepared according to the Phenomenex EZ:faast™ kit's manual, with the following modifications: prior to amino acid extraction and derivatization, 20 μL of each internal standard solution containing 100 μmol/L Phe-d5 and 20 μmol/L Tyr-d4 (in 50 mmol/L HCl) were added to 40 μL of sample lysate. Using the kit's reagents, the amino acids are derivatized with propyl chloroformate resulting in the addition of a propyl formate at the amine moiety and a propyl group at the carboxylic end of the amino acids, respectively. The hydroxy group of Tyr is also derivatized by the addition of a propyl formate group.
Instrumentation For RP (reversed phase)-HPLC separation of amino acids, a 250×2 mm C18 column (Phenomenex EZ:faast™) was used. The derivatized amino acids were separated using the following program: (i) isocratic flow 75% solvent B for 6 min; (ii) linear gradient from 75% to 95% solvent B (v/v) in 9 min; (iii) linear gradient from 95% to 100% solvent B in 0.1 min; (iv) isocratic flow 100% solvent B for 3 min; (v) linear gradient from 100% to 75% solvent B in 0.1 min; (vi) isocratic flow 75% solvent B for 2 min. Solvents A and B were 10 mmol/L ammonium formate in $H_2O$ and 10 nmol/L ammonium formate in methanol, respectively. Flow rate was 150 μL/min and the injection volume was 10 μL. A PerkinElmer SCIEX API 2000 LC-ESI-MSMS system equipped with a PerkinElmer Series 200 autosampler and two PerkinElmer Series 200 micro pumps were used for LC-ESI-MSMS analysis. Amino acids were acquired using the multiple reaction mode (MRM) positive ion mode, with the following transitions: 294→206 (Phe), 299→211 (Phe-d5), 302→214 (Phe-d8), 396→308 (Tyr) and 400→312 (Tyr-d4). The dwell time was 500 ms. Mass spectra were acquired in the time range of 6 to 20 min.

Results:
Reduction of Brain Phe Level

Figure 5:
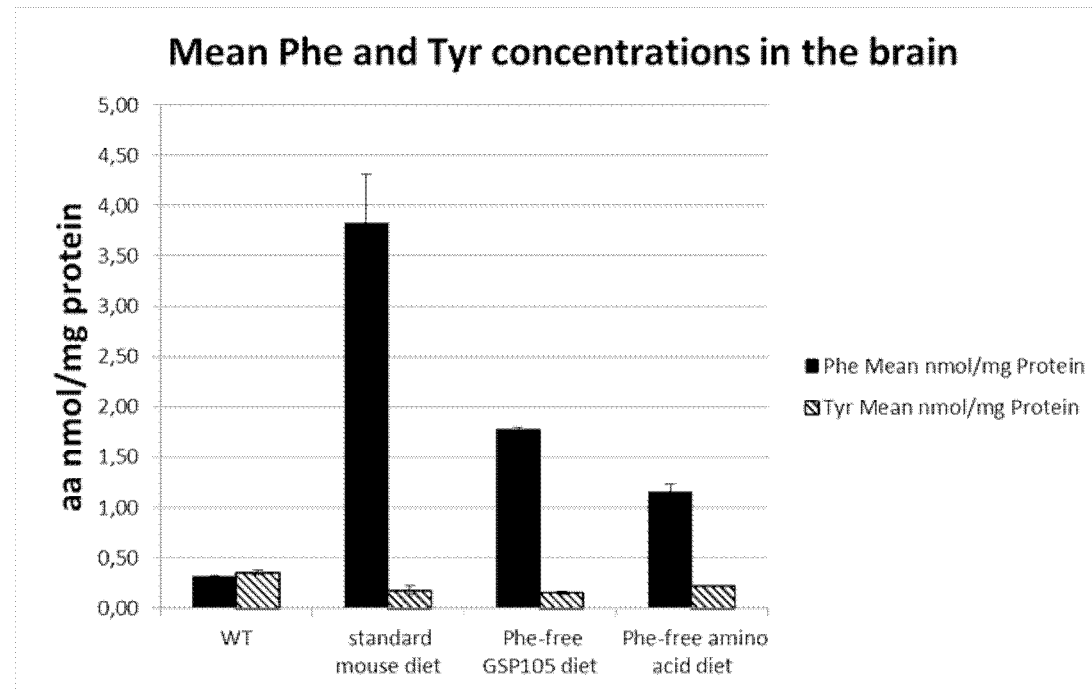
FIG. 5 shows the mean Phe and Tyr concentrations in the brain of wild type (WT) mice and PKU mice treated with standard mouse diet, the Phe-free GSP105 protein diet or the Phe-free amino acid diet.

FIG. 5 shows the mean Phe and Tyr concentrations in the brain of wild type (WT) mice, PKU mice treated with the standard mouse diet, the Phe-free GSP105 protein diet or the Phe-free amino acid diet.

Mean concentrations of the amino acids phenylalanine and tyrosine in the brain of wild type (WT) mice were approximately the same (0.31 nmol Phe/mg protein; 0.36 nmol Tyr/mg protein) (FIG. 5) resembling the situation in healthy humans.

On contrast, the mean Phe concentration in the brain of PKU mice fed with the standard mouse diet (group 1) showed a 10-fold increase (Phe 3.82 nmol/mg protein) with a low mean Tyr concentration of 0.18 nmol/mg protein, corresponding to the situation of un-treated PKU patients.

Feeding of the Phe-free GSP105 protein diet (group 2) led to a 50% reduction of the mean brain-Phe concentration (Phe 1.78 nmol/mg protein) compared to the feeding of the standard mouse diet, while the mean Tyr concentration kept low (0.15 nmol/mg protein).

The lowest mean brain-Phe level and the highest mean brain-Tyr level were reached with the Phe-free amino acid diet in group 3 (Phe 1.16 nmol/mg protein; 0.22 nmol/mg protein).

The results of the analysis of the Phe- and Tyr-concentrations in the brain of WT mice as well as treated and un-treated PKU mice matched with the corresponding blood-Phe and blood-Tyr levels in the different animal feeding groups (FIGS. 2 and 4).

The strongest decrease of the brain-Phe concentration was obtained with the Phe-free amino acid diet. Taking into account that the influence of a low Phe-diet on cerebral Phe levels is delayed and not as steep as the influence on the blood-Phe concentration, we assume a further reduction of Phe in the brain within a prolonged feeding period with the Phe-free GSP105 protein diet. This hypothesis is based on the observation that blood Phe levels within this group approximated the blood-Phe concentrations of mice fed with the Phe-free amino acid diet after a feeding period of 28 days.

Mean Phe/Tyr Ratio in the Brain

Figure 6:
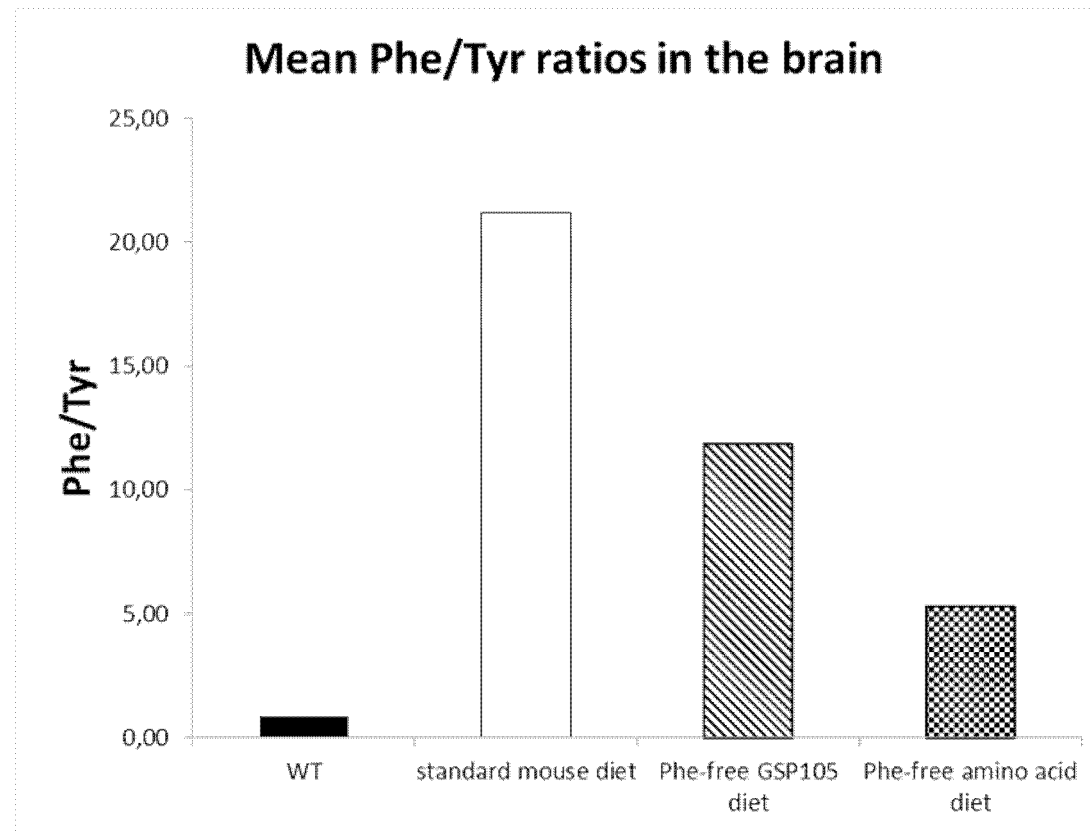
FIG. 6 shows the mean Phe/Tyr ratios in the brain of WT mice and PKU mice treated with standard mouse diet, the Phe-free GSP105 protein diet or the Phe-free amino acid diet.

FIG. 6 shows the mean Phe/Tyr ratios in the brain of WT mice, PKU mice treated with the standard mouse diet, the Phe-free GSP105 protein diet or the Phe-free amino acid diet.

The Phe-free amino acid diet resulted in the lowest Phe/Tyr ratio in the brain of PKU mice (FIG. 6, checked column), followed by the Phe-free GSP105 protein diet (FIG. 6, diagonally striped column). The PKU mice on the standard mouse diet are depicted in FIG. 6 as white column with black frame. The Phe/Tyr ratio is significantly better than for the PKU mice on the standard diet. The Phe-free GSP105 protein diet could be improved by reducing the amount of Phe contaminant from the purified recombinant dietary protein GSP105, and/or by supplementation of crystalline tyrosine, as used in the Phe-free amino acid diet, or addition of a tyrosine containing designer tail.

The invention claimed is:

1. A recombinant dietary protein comprising a polypeptide sequence that is at least 90% identical to SEQ ID NO 2 for treating a disorder characterized by accumulation of phenylalanine in a body of a subject, wherein said protein comprises (i) all of histidine, arginine, isoleucine, leucine, lysine, methionine, threonine, tryptophan, and valine, and (ii) no phenylalanine.

2. The recombinant dietary protein of claim 1, wherein the polypeptide sequence is at least 96% identical to SEQ ID NO 2.

3. The recombinant dietary protein of claim 1, wherein the protein further comprises one or more additional protein sequences, wherein the additional protein sequence is a purification tag or label.

4. The recombinant dietary protein of claim 3, wherein the additional protein sequence is a polypeptide tag comprising the amino acid sequence SEQ ID NO 3.

5. A vector comprising a nucleic acid sequence encoding the recombinant dietary protein of claim 1.

6. A recombinant microorganism comprising the vector of claim 5.

7. The recombinant microorganism of claim 6, wherein the microorganism is selected from the group consisting of Escherichia, Klebsiella, Pseudomonas, Xanthomonas, Bacillus, Staphylococcus, Saccharomyces, Corynebacterium, Streptomyces, Salmonella, Aspergillus, Gluconobacter, Mycobacterium, Actinomycetes, Caulobacter, Pichia, Corynebacterium glutamicum, Saccharomyces cerevisiae, Clostridium botulinum, Flavobacterium heparinum, Lactococcus lactis, Methylobacterium extorquens, Pseudoalteromonas haloplanktis, Ralstonia eutropha, Neurospora crassa, Arxula adeninivorans, Hansenula polymorpha, Kluyveromyces lactis, Zygosaccharomyves bailii, Pseudomonas fluorescens, Bacillus subtilis and Bacillus megaterium.

8. The recombinant microorganism of claim 7, wherein said microorganism is of the species Bacillus or Pseudomonas.

9. The recombinant microorganism of claim 8, wherein said microorganism is Bacillus subtilis or Pseudomonas fluorescens.

10. A method of producing the recombinant dietary protein encoded by the nucleic acid sequence of the vector of the recombinant microorganism of claim 6, the method comprising culturing the recombinant microorganism of claim 6 under conditions suitable for production of the dietary protein by the recombinant microorganism.

11. A dietary composition comprising the recombinant dietary protein according to claim 1.

12. A method of treating a disorder characterized by accumulation of phenylalanine in a body of a subject, the method comprising administering to the subject the dietary protein of claim 1 in an amount sufficient to treat the disorder.

13. The method of claim 12, wherein the disorder is hyperphenylalaninemia.

14. The method of claim 12, wherein the disorder is phenylketonuria.

15. A medicament and/or food for the management of a disorder characterized by accumulation of phenylalanine in the body comprising the dietary protein of claim 1.

16. The recombinant dietary protein of claim 1, wherein the polypeptide sequence is at least 97% identical to SEQ ID NO 2.

17. The recombinant dietary protein of claim 1, wherein the polypeptide sequence is at least 98% identical to SEQ ID NO 2.

18. The dietary composition of claim 11 comprising no more than 0.1 g phenylalanine per 100 g total protein.

\* \* \* \* \*